United States Patent [19]

Gelorme et al.

[11] Patent Number: 5,317,081
[45] Date of Patent: May 31, 1994

[54] MICROWAVE PROCESSING

[75] Inventors: Jeffrey D. Gelorme, Plainville, Conn.; David A. Lewis, Carmel, N.Y.; Jane M. Shaw, Ridgefield, Conn.

[73] Assignee: International Business Machines Corporation, Armonk, N.Y.

[21] Appl. No.: 799,378

[22] Filed: Nov. 27, 1991

Related U.S. Application Data

[62] Division of Ser. No. 551,716, Jul. 11, 1990.

[51] Int. Cl.$^5$ .................. C08G 69/26; C08G 73/10; B05D 5/12
[52] U.S. Cl. .................. 528/353; 528/125; 528/126; 528/128; 528/170; 528/188; 528/220; 528/229; 528/351; 522/173; 522/174; 522/176; 428/458; 428/473.5; 427/96; 427/124; 427/553; 427/508
[58] Field of Search .......... 528/125, 128, 126, 170, 528/188, 220, 229, 351, 353; 428/473.5, 458; 427/12, 96, 45.1, 124; 522/174, 173, 176; 430/270

[56] References Cited

U.S. PATENT DOCUMENTS

| | | | |
|---|---|---|---|
| 3,458,808 | 7/1969 | Agdur | 324/633 |
| 3,845,018 | 10/1974 | Bilow et al. | 528/226 |
| 3,864,309 | 2/1975 | Bilow | 528/183 |
| 3,879,349 | 4/1975 | Bilow | 528/226 |
| 4,108,836 | 8/1978 | Bilow | 528/128 |
| 4,255,313 | 3/1981 | Antonoplos et al. | 528/128 |
| 4,299,750 | 11/1981 | Antonoplos et al. | 528/128 |
| 4,305,796 | 12/1981 | Gagliani et al. | 521/185 |
| 4,315,076 | 2/1982 | Gagliani et al. | 521/185 |
| 4,315,077 | 2/1982 | Gagliani et al. | 521/185 |
| 4,315,080 | 2/1982 | Gagliani et al. | 521/185 |
| 4,316,844 | 2/1982 | Waitkus et al. | 528/229 |

(List continued on next page.)

FOREIGN PATENT DOCUMENTS 0048119 3/1982 European Pat. Off. .
2552613 3/1985 France .

OTHER PUBLICATIONS

Lewis et al., "Cure Kinetics and Mechanical Behavior Of Electromagnetically Processed Polyimides", Dept. of Chemistry and Polymer Materials and Interfaces Laboratory, Virginia Polytechnic Institute and State University, Blacksburg, Vir.

Primary Examiner—John Kight, III
Assistant Examiner—P. Hampton-Hightower
Attorney, Agent, or Firm—Scully, Scott, Murphy & Presser

[57] ABSTRACT

A method and apparatus are disclosed for conducting a physical process and a chemical reaction by exposing a material containing a volatile substance to microwave radiation where the morphology of said material will change when exposed to such radiation. The power of said radiation is adjusted over time as the morphology of the material changes to maximize the effect of the radiation in order to produce a product in a minimum amount of time that is substantially free of said volatile substance.

The method and apparatus can also be used to conduct such a process or reaction with materials that do not contain a volatile material.

In one embodiment a method and apparatus are disclosed for manufacturing a polyimide from a precursor in a solvent by exposing the precursor to microwave radiation in a tuneable microwave resonant cavity that is tuned during imidization to achieve critical coupling of the system. Microwave power is controlled to remove the solvent and obtain the desired level of reaction. Processing time has been reduced thirty fold as compared to conventional thermal methods.

28 Claims, 4 Drawing Sheets

U.S. PATENT DOCUMENTS

| | | | |
|---|---|---|---|
| 4,319,000 | 3/1982 | Gagliani et al. | 521/185 |
| 4,346,182 | 8/1982 | Gagliani et al. | 521/185 |
| 4,355,120 | 10/1982 | Gagliani et al. | 521/185 |
| 4,360,604 | 11/1982 | Gagliani et al. | 521/185 |
| 4,361,453 | 11/1982 | Gagliani et al. | 521/185 |
| 4,363,690 | 12/1982 | Gagliani et al. | 521/185 |
| 4,363,883 | 12/1982 | Gagliani et al. | 521/185 |
| 4,367,296 | 1/1983 | Gagliani et al. | 521/185 |
| 4,439,381 | 5/1984 | Gagliani et al. | 521/185 |
| 4,556,682 | 12/1985 | Gagliani | 521/77 |
| 4,566,804 | 1/1986 | Collins et al. | 374/14 |
| 4,585,668 | 4/1986 | Asmussen et al. | 427/45.1 |
| 4,606,650 | 8/1986 | Harris | 374/14 |
| 4,654,223 | 3/1987 | Araps et al. | 430/319 |
| 4,656,050 | 4/1987 | Araps et al. | 428/473.5 |
| 4,681,654 | 7/1987 | Clementi et al. | 156/630 |
| 4,681,996 | 7/1987 | Collins et al. | 374/14 |
| 4,749,621 | 6/1988 | Araps et al. | 428/473.5 |
| 4,767,902 | 8/1988 | Palaith et al. | 156/89 |
| 4,792,772 | 12/1988 | Asmussen | 333/230 |
| 4,822,537 | 4/1989 | Lanier et al. | 521/185 |
| 4,871,619 | 10/1989 | Araps et al. | 428/473.5 |
| 4,885,527 | 12/1989 | Lacombe et al. | 324/636 |

MICROWAVE PROCESSING

This is a divisional of copending application Ser. No. 551,716, filed on Jul. 11, 1990, pending.

TECHNICAL FIELD

The technical field of the invention is the application of microwave radiation to physical processes and chemical reactions such as the preparation of polyimide polymers from polyamic acid precursors dissolved in a solvent in which the solvent is volatilized by microwave radiation followed by imidization of the precursor by microwave radiation. The reaction of these precursors to form the polymers is well known in the art. The invention in one aspect is directed to a new method for the application of microwave radiation to the precursor to control the degree and rate of the imidization and to accurately determine the end point of or degree of imidization by an in situ non-destructive testing method.

PRIOR ART

Lewis et al. *Polymer Preprints*, Vol. 29, No. 1 pp. 174-75, 1988 describe the cure kinetics and mechanical behavior of electromagnetically processed polyimides in which a BTDA and DDS polyimide is imidized in solution consisting of N-methylpyrolidone (NMP), cyclohexylpyrolidone (CHP) (4:1) in a tuneable microwave cavity, the imidization of the polyamic acid intermediate being conducted isothermally by detuning the cavity which decreases the electric field intensity in the region of the sample. Anywhere from about 20 to about 80% conversion of the polyamic acid to the polyimide was obtained using this method. It was observed that by employing the method described that the rate of imidization was increased either due to an effect of the electromagnetic radiation on the NMP coordinated with the amic acid or a very localized temperature rise due to directed absorption of the radiation. A film was never formed using microwave radiation with this material.

The conversion of PMDA-ODA type unimidized materials into a partially cured polyimide is described by Clementi et al. U.S. Pat. No. 4,681,654 (par. bridging col. 3 and 4) so that less than approximately 50 percent of the composition is imidized. This is effected by drying the unimidized mixture using either an infrared heater, convection oven, microwave oven or other such heating equipment.

Polyimide foams have been prepared as described by Gagliani et al. in U.S. Pat. Nos. 4,305,796 and 4,439,381 based on equimolar mixtures of a lower alkyl half ester of BTDA and two primary diamines.

Foaming of this mixture proceeds by exposing it to microwave radiation to release the by-products of the imidization of these components i.e. a lower alkanol and water. Complete imidization, however, was not obtained with the application of microwave radiation. The lower alkanol and water act as blowing agents as noted by Lanier et al. U.S. Pat. No. 4,822,537 (col. 9 lines 43-47).

Gagliani et al. exposes a polyimide precursor to microwave radiate to initiate foaming and partial curing i.e. partial imidization of the mixture into a foam. Preferably, the mixture is preheated before it is exposed to microwave radiation which contributes to a higher foam rise. (Gagliani '796; col. 5 lines 13-16.) Gagliani et al. also note that steady application of microwave energy is not required and post or cyclic exposure of the mixture to the microwave energy most likely will produce superior results. The microwave energy pulses and intervals between are in the order of 60 and 20 seconds respectively. (Gagliani et al. '796; col. 5 lines, 20-25; '381 col. 5, lines 15-20).

Microwave radiation as employed in the prior art effects only a partial imidization of the polyamic acid to polyimide as noted by Clementi et al. (U.S. Pat. No. 4,681,655; par. bridging col. 3-4 and col. 7, lines 36-53) and Gagliani et al. (U.S. Pat. No. 4,305,796; col. 6 lines 43-50; U.S. Pat. No. 4,439,381; col. 5, lines 61-67). Clementi et al.(ibid.) note the polyamic acid is partially imidized to an "A" stage such that less than approximately 50 percent of the precursor is imidized to the polyimide and the "A" stage polyimide is then cured further to a "C" stage at 360°-400° C. for approximately 30 minutes using non-microwave heating. Gagliani et al. (ibid.) teach that the partially cured polyimide foam is heated in a circulating air oven at a temperature of 500°-550° F. for 30-200 minutes to complete the Lanier et al. (supra) discloses a method for manufacturing polyimide foams employing mixtures similar to Gagliani et al. (supra) but also discloses the use of organic or inorganic blowing agents (U.S. Pat. No. 4,822,537, col. 9 lines 43-60). As with Gagliani et al., Lanier et al. preheat the mixture prior to exposing to microwave radiation (U.S. Pat. No. 4,822,537 col. 2 lines 63-66).

Asmussen in U.S. Pat. Nos. 4,792,772; 4,727,293; 4,630,566; 4,585,668 and 4,507,588 describes tuneable microwave cavities for generating plasmas but does not describe utilizing them for chemical reactions or drying reactions nor do they contain means for removing vapor from the chamber.

The various types of polyimides and polyimide precursors known in the art which this invention deals with are described in Kirk-Othmer *The Encyclopedia of Chemical Technology*, 3rd Edition vol. 18, pp. 704-19 including the various literature and patent references set forth on pp. 718-19, all of which are incorporated herein by reference.

SUMMARY OF THE INVENTION

The present invention comprises the application of microwave radiation to physical processes and chemical reactions in a controlled manner so as to obtain products from these processes that are substantially defect free in a minimum amount of time.

The microwave radiation frequency is selected so that it will be absorbed by the sample and the electric field strength E is also selected between minimum (E min) and maximum (E max) values which are empirically measured so that the product obtained when irradiated at an electric field strength E will possess optimum properties. This method is applicable to physical processes such as drying samples e.g. removing solvent from polyimide precursors or water from ceramic materials and/or chemical processes such as the imidization of polyimide precursors and the curing of ceramic materials.

The present invention also comprises applying microwave radiation to such physical processes and chemical reactions in a tuneable microwave cavity so that microwave power is varied over time, based on the quality of cure factor "Z" (defined hereafter) in such a way to obtain a substantially defect free product in a minimum amount of time. The Z factor or cure fraction refers to the quality of cure or completion of the reaction whether a physical process or a chemical reaction in which the invention is employed.

Microwave radiation is applied to either a physical process or chemical reaction in order to obtain a predetermined value for Z or quality of cure factor which, in a tuneable microwave cavity, is a function of the Q factor and temperature of the system. The Q factor (sometimes referred to as the quality factor), in turn is based on the resonance of the microwave radiation applied to the process and in turn is measured by a comparison of the applied microwave power and reflected microwave power in the system. Where reflected microwave power is minimized (which is to say that a maximum amount of microwave power is absorbed by the sample being dried or cured and a minimum amount of microwave power is reflected by the system) the quality factor or Q of the system is obtained. Since the Q factor varies with temperature and the change of physical state of the system (i.e. the change of the dielectric constant due to chemical and/or physical changes) the Q factor alone will not by itself provide a sufficient basis for obtaining maximum results from the application of microwave radiation to either the chemical reaction or physical process. Accordingly, the Z of the system which is a function of the quality factor Q and the temperature of the system is employed according to the present invention so as to provide an indication of how microwave power is to be varied over time (based on Z) in such a way to produce a product that has been processed to a precise predetermined degree in a minimum amount of time. Microwave power is therefore varied over time based on Z in such a way to produce a substantially defect free material in a minimum amount of time where this power is applied either in a physical process (e.g. drying or solvent removal) or a chemical process (e.g. polymerization or curing a ceramic material).

Utilization of a microwave apparatus that comprises a tuneable microwave resonant cavity that is tuned during the imidization to achieve resonance of the system is essential to the practice of one embodiment of the invention. The Q factor is determined for the system (which is based on the microwave apparatus, e.g. the and the precursor and/or polyimide depending on the degree of imidization) and indicates when the precursor is substantially completely imidized or any degree of partial imidization is reached. The imidization therefore may be controlled to a reasonably precise predetermined end point and measured without removing the polyimide from the microwave apparatus or employing destructive testing methods for measuring the degree of imidization to the polyimide.

By employing the method of the invention a thirty fold reduction of the processing time has been obtained.

The invention may be employed in processes for coating integrated circuits such as microcircuits with polyimide films or any other substrate such as a semiconductor substrate, an electrical insulator substrate or any combination thereof, including metal and/or electrical wiring within the insulator substrate.

DETAILED DESCRIPTION OF THE INVENTION

Figure 1:
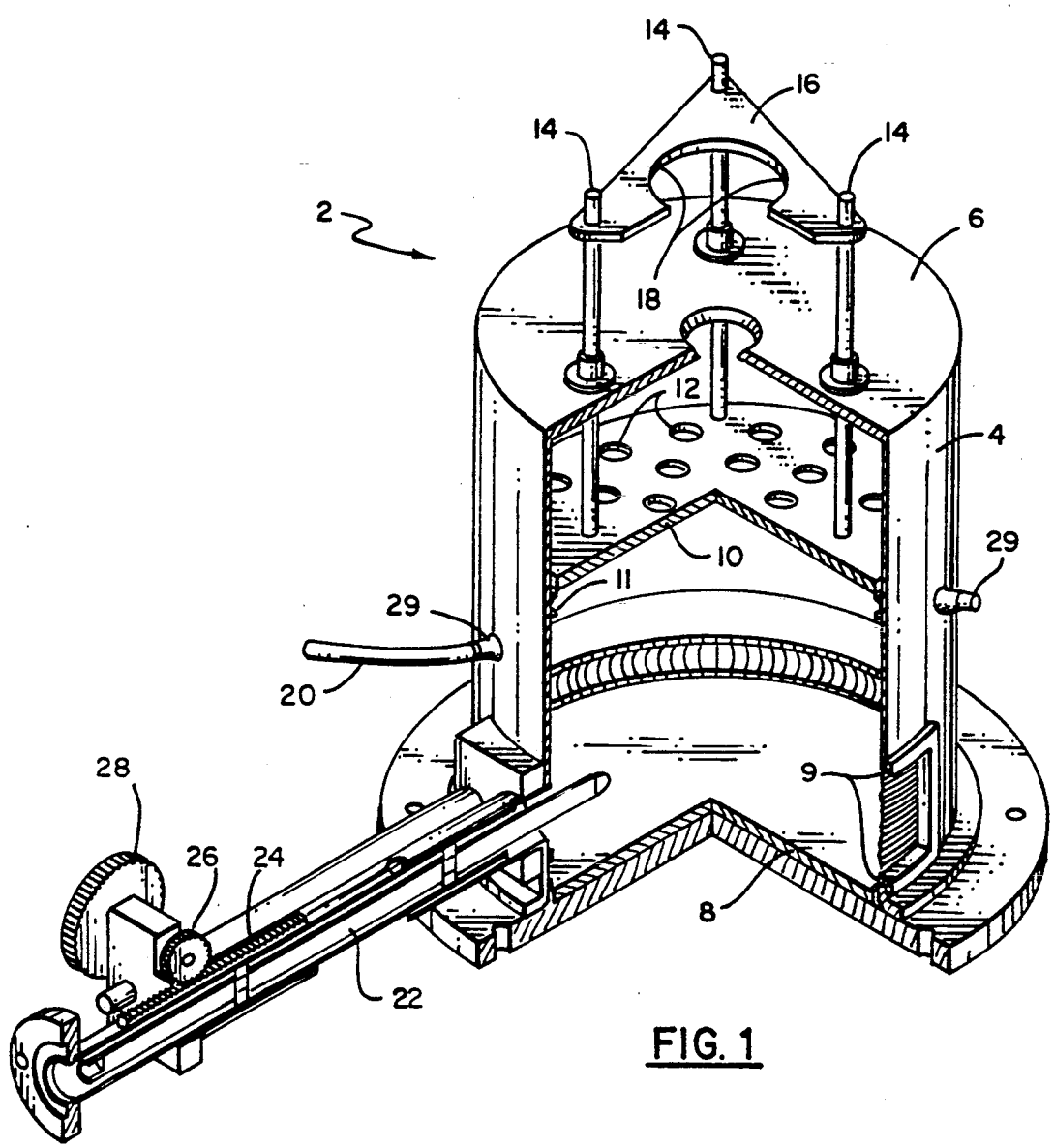
FIG. 1 comprises a three dimensional view of a tuneable microwave cavity processing system according to one embodiment of the invention.

In the fabrication of integrated circuits such as microcircuits, insulating layers are applied over the circuits or utilized in sandwich construction. These layers in some applications comprise polyimide films. The conventional polyimides utilized in these respects are prepared from precursors that contain polyamic acid groups, polyamic ester groups or combinations thereof, the precursors in turn being prepared by the reaction of a dianhydride and diamine or a diester-diacid dichloride and diamine. The precursor that is produced is soluble in common organic solvents and when dissolved, can be applied to various substrates as a coating. After the substrate is coated the solvent is removed, usually by the application of heat to the coated substrate and with continued heating, the precursor is converted into a polyimide film with the evolution of water as a product of the imidization reaction. The polyimide film obtained is not readily soluble in conventional solvents, is extremely strong and can be made to adhere to most substrates. Because of the outstanding physical properties of polyimide resins, they have been widely used in many coating applications. One of the disadvantages of polyimides in all of the foregoing reactions is the cure time which typically in thin film applications can be as high as ten to twelve hours.

As noted, the precursor is converted to the polyimide with the evolution of water as a by-product of reaction. This imidization usually begins at about 150° C. whereas temperatures upwards of about 300° C. are required to complete the process which is sometimes referred to as dehydration.

In curing polyamic acid by this dehydration process to form the polyimide polymer, care has to be taken so that even heating is effected throughout the cross-section of polyamic acid being converted which is not always easy to achieve. For example, when films of polyamic acid are exposed to heat in conventional ovens, the film cures from the outer most surface inwardly and if the curing process proceeds at too high a rate, the outer surface of the film will be (i) cured significantly faster than the center, possibly resulting in void formation, (ii) or result in inferior mechanical properties such as reduced modulus, enhanced swelling, solvent uptake and CTE (coefficient of thermal expansion).

The prior art contains general disclosures regarding the use of microwave radiation to convert polyamic acid precursors to polyimides (Gagliani et al. and Clementi et al. supra), however, as a practical matter greater than 50% conversion of the precursor to the polyimide has not been obtained.

It is believed that these problems encountered with microwave curing of polyamic acids to polyimides is due in large measure to the microwave device employed. The microwave apparatus conventionally utilized in this regard is similar in operation to a "home microwave" i.e. a large, multimode chamber with one or more magnetrons coupling microwave radiation into the chamber. These systems typically operate at full power which is regulated by turning it on or off, resulting in a form of "pulsed" radiation treatment. This apparatus has the disadvantage of non-uniform microwave fields which vary spatially with the movement and/or curing of the part. This can result in non-uniform curing on a small level, resulting in enhanced stress in the film, since these materials shrink on curing. In addition, solvent evaporation is difficult to control resulting in poor film quality and it is difficult in such an arrangement to obtain sufficiently high electric field strengths (power density) to obtain full or substantially full cure of the polyimide. Gagliani. et al. (supra) even describe the use of short bursts of microwave radiation in this regard.

Thus the prior art solution to the difficulties encountered with microwave curing was to employ the microwave process only for partial imidization of polyamic acids to polyimides and subsequently heating the product obtained by means other than microwave radiation.

One of the other difficulties encountered in the prior art was that in situ test means were not available to determine the degree of imidization of the polyamic acid to polyimide. The product had to be removed from the imidizing reaction milieu and tested, either by wet analysis to determine the carboxylic acid groups in the product or by other test methods such as FTIR spectroscopy and the like.

These prior art methods employing microwave radiation also did not lend themselves to the precise control of the rate and degree of imidization of polyamic acid to polyimides over a range from partial imidization to substantially complete imidization in such a way as to optimize the mechanical properties of the imidized product.

There has also been no disclosure in the prior art of a method for exposing a polyimide precursor material to microwave radiation when the precursor has been placed on a substrate such as metal containing PC boards or various metal oxides such as alumina with metal wiring and pads and metal over Kapton (trademark) polyimide. It is usually assumed that arcing between the metal pads would result and damage the pads and dielectric material.

Accordingly, it is an object of the present invention to overcome these and other difficulties encountered in the prior art.

It is therefore an object of the present invention to provide a novel method for the application of microwave power to promote a physical process or chemical reaction to obtain a substantially defect free product in a amount of time.

It is a further object of the present invention to provide a process for applying microwave power to a physical process or a chemical reaction at an electric field strength between E max and E min to maximize the effect of microwave radiation in producing a substantially defect free product in a minimum amount of time.

It is a further object of the present invention to provide a film of a polyimide precursor of a predetermined thickness, exposing said film to microwave radiation having a wavelength sufficient to be absorbed by the film wherein the electric field of the radiation has a value sufficient to cure the precursor to a substantially defect free polyimide film in a minimum amount of time.

It is a further object of the present invention to provide a method for the imidization of a polyamic acid precursor dissolved in a solvent to substantially remove the solvent without causing the precursor to foam or develop voids therein by applying microwave radiation to the precursor in such a manner so as to obtain substantially complete removal of the solvent in a minimum amount of time.

It is a further object of the present invention to remove solvent from such a polyamic acid precursor as described above, and to further apply microwave radiation to the precursor to obtain an imidized product that is substantially defect free in a minimum amount of time.

It is a further object of the present invention to provide a method and apparatus for manufacturing a polyimide by irradiating a polyimide precursor containing polyamic acid groups with microwave radiation in a microwave apparatus in which the degree of imidization of the precursor to the polyimide is not only controlled over a range of from partial imidization to substantially complete imidization but also the apparatus employed can be utilized for the in situ measurement of the degree of imidization of the precursor to a polyimide without removing the polyimide from the microwave apparatus.

It is a further object of the present invention to provide a method and apparatus for manufacturing a polyimide from a precursor in a microwave apparatus where such apparatus comprises a tuneable microwave resonant cavity means.

It is also an object of the present invention to provide such a method as well as a microwave apparatus for imidizing such a precursor to a polyimide where vapor from the process is removed so that it does not have any adverse effects on the surface of the part processed, especially where there is uncured precursor on the bottom of the substrate that also has to be imidized.

It is a further object of the present invention to provide a method and apparatus for imidizing such a precursor to a polyimide supported on a substrate such as an integrated circuit, a microcircuit, an electrical conductor such as a metal substrate, a semiconductor substrate or a nonelectrical conducting substrate such as a ceramic material including those noted herein.

It is also an object of the present invention to by exposing such precursors to microwave radiation employing a microwave apparatus with a variable power output and steady state (non-interrupted) microwave radiation.

These and other objects have been achieved according to the present invention which is more fully described in the written description and claims that follow as well as the attached drawings.

The present invention in one embodiment comprises a method and apparatus for manufacturing a polyimide by introducing a polyimide precursor containing polyamic acid groups, polyamic ester groups or the equivalents thereof into a microwave apparatus by which microwave radiation may e applied to the precursor. The precursor in combination with the microwave apparatus comprises a system. The precursor is then irradiated with the microwave radiation to convert it to the polyimide. The radiation may also be employed to initially remove solvent from the precursor in such a way to avoid imperfections in the precursor such as voids, surface irregularities (e.g. pits) and the like. One feature of the microwave apparatus is that it comprises a tuneable microwave resonant cavity means; another feature of the apparatus is it employs a variable power output whereby the power of the microwave radiation during the imidization is adjusted to control the degree and rate of imidization of the precursor.

It has also been discovered according to the present invention that the Q factor of the system can be monitored during imidization. The process cycle can be stopped at any one of several Q factor temperature combinations, depending on the degree of imidization that is to be achieved from freshly cast precursor in solvent up to substantially complete cure.

Figure 4:
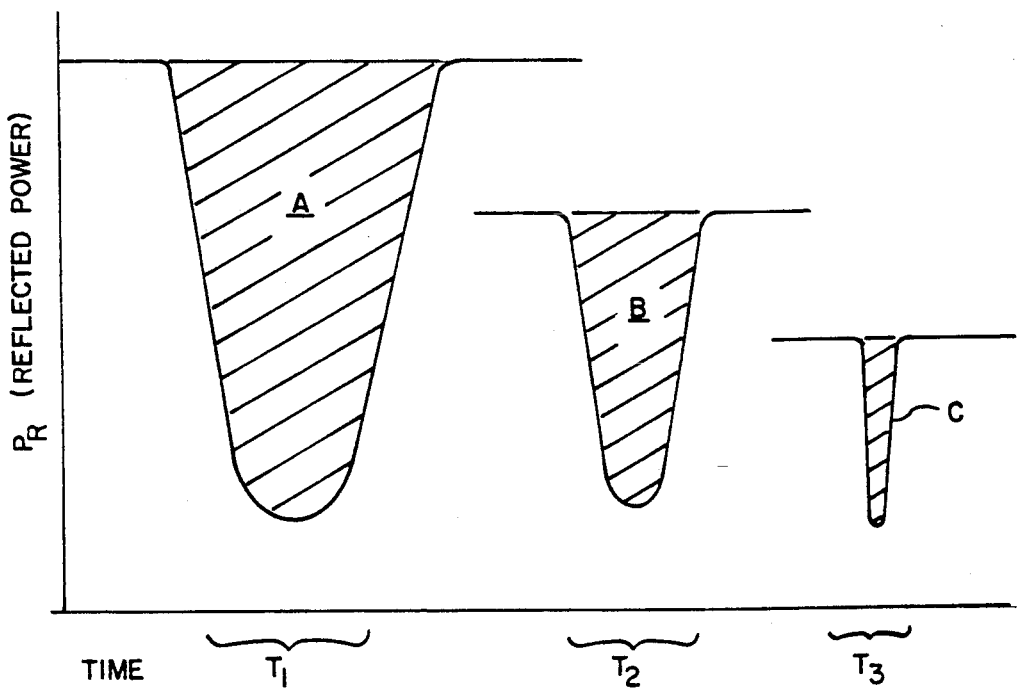
FIG. 4 comprises a plot of the reflected microwave power against the height of the cavity of the apparatus of FIG. 1, wherein the Q factor (i.e. quality factor) for the system is the reciprocal of the width at half height of the resonant dip obtained by monitoring the microwave power reflected from the coupling to the cavity.

The Q factor, as that expression is used throughout this specification, is the quality factor of the microwave cavity and is determined from the reciprocal of the width at half height of the resonant dip obtained as shown in FIG. 4 by monitoring the microwave power reflected from the power coupling to the cavity as the cavity height is varied. This is also illustrated in FIG. 4 where reflected power is plotted against height of the cavity.

In FIG. 4, reflected power is plotted along the Y axis and cavity height along the X axis for a single precursor containing polyamic acid (or ester) that is exposed to microwave radiation in such apparatus. Since the precursor absorbs energy in the initial phases of the process, the width of the resonance curve (FIG. 4) will be relatively large giving a lower Q factor. As the imidization proceeds and solvent removed, less microwave power is absorbed by the sample resulting in a reduction in the width of the resonant dip in FIG. 4, thereby corresponding to an increase in Q. Since the absorbtion of microwave energy is temperature dependent, as governed by $\Sigma$(the loss factor) and also the physical state of the film (e.g. glass or rubber) the Q factor will also be temperature dependent.

In each one of the time intervals, $T_1$, $T_2$ and $T_3$ in FIG. 4 the microwave resonance of the tuneable cavity of the apparatus changes because the structure of the polyamic acid changes i.e. the polyamic acid/solvent combination is converted to a combination having mostly polyamic acid, some polyimide formation and some residual solvent to a material which is substantially solvent free and substantially completely polymerized to a polyimide with various degrees of imidization and solvent removal between the two extremes. This causes changes in the resonance of the cavity which is compensated for by tuning the cavity to maximum resonance (critical coupling) which corresponds to minimum reflected power (or zero reflected power). The tuning of the cavity is effected by moving the short 10 of the microwave apparatus upwardly or downwardly during the process and the coupling probe 22 in and out of the cavity.

As an example, power levels P1–P4 are applied to a polyamic acid precursor dissolved in solvent which is coated on a plate that is positioned on bottom wall 8 in the tuneable cavity 2 of FIG. 1. Power is applied for a period of four time intervals to develop Q values of 8,000, 9,500, 10,000 and 10,500 to initially drive solvent off from the film followed by partial imidization going up through substantially complete imidization. These steps may be summarized in the following Table 1.

| Power | Q | Temp | |
|---|---|---|---|
| P1 | 8,000 | 130–150 | Begin driving off solvent |
| P2 | 9,500 | 170 | More solvent driven off |
| P3 | 10,000 | 180 | Begin imidization, drive off residual solvent. |
| P4 | 10,500 | 250–350 | Complete imidization |

The Q-factor coupled with the sample temperature provides a "quality of cure" factor "Z" which is a single value that describes the state of cure of the system (as determined by IR and the like). The analytical relationship between Z, Q and temperature can be determined from a series of measurements of Q temperature and the degree of conversion of the precursor to the polyamide as determined by FTIR and equivalents thereof. The Z factor therefore is obtained by measuring values of Q at a definite temperature and a definite degree of conversion and is an absolute value that can be measured for any reactants employing any microwave device.

The Z factors can then be utilized to specifically indicate the degree of imidization to a polyimide of any subsequent run whither to obtain partial imidization or substantially complete imidization and thereby provides a method for the measurement of the degree of imidization without removing the material from the microwave apparatus. This is a non-destructive testing method for determining in situ the degree of imidization, but is not limited to imidization reactions.

Thus the invention is applicable to any process that absorbs microwave energy. The power of the microwave device is varied over time based on Z in such a way to produce a substantially precise end point of the reaction in a minimum amount of time to obtain a product of the desired quality, e.g. one free of voids and having substantial uniform physical and electrical properties. When microwave energy is applied according to the present invention for the manufacture of polymeric films which can be foamed either because of the entrapment of products of conversion of polyamic acid or ester precursors to polyimides) or because the precursor is employed in combination with a solvent, the microwave power is varied over time based on Z in such a way to produce a substantially defect free film in minimum time.

Although the method of the invention has been described with reference to the manufacture of polyimide films it is also applicable to the manufacture of any compounds and the sample or reaction milieu will absorb microwave energy whether for the manufacture of organic or inorganic compounds. For example, the process of the invention may be employed for the manufacture of laminates based on polyesters, epoxies, phenolics, acrylates and the like or the manufacture of such polymeric materials in non-laminate structures. Similarly, ceramic materials may also be dried and/or reacted employing the method of the invention.

The process of the invention can also be employed for removing solvents from substrates not only where the solvent in the precursor is removed by a controlled application of microwave power prior to curing but also for drying other materials such as removing the solvent from a photoresist to a precise level, removing solvent or the liquid reaction medium from the by-products of physical processes or chemical reactions especially those in which solvent removal promotes the growth of crystalline materials and the like.

Although the invention has been described with reference of the system can be obtained by varying the cavity height or the radiation frequency or the position of the probe 22 in the cavity to match the impedance of the cavity, other systems which do not employ a microwave resonant cavity can also be employed and the process of the invention utilized.

Figure 5:
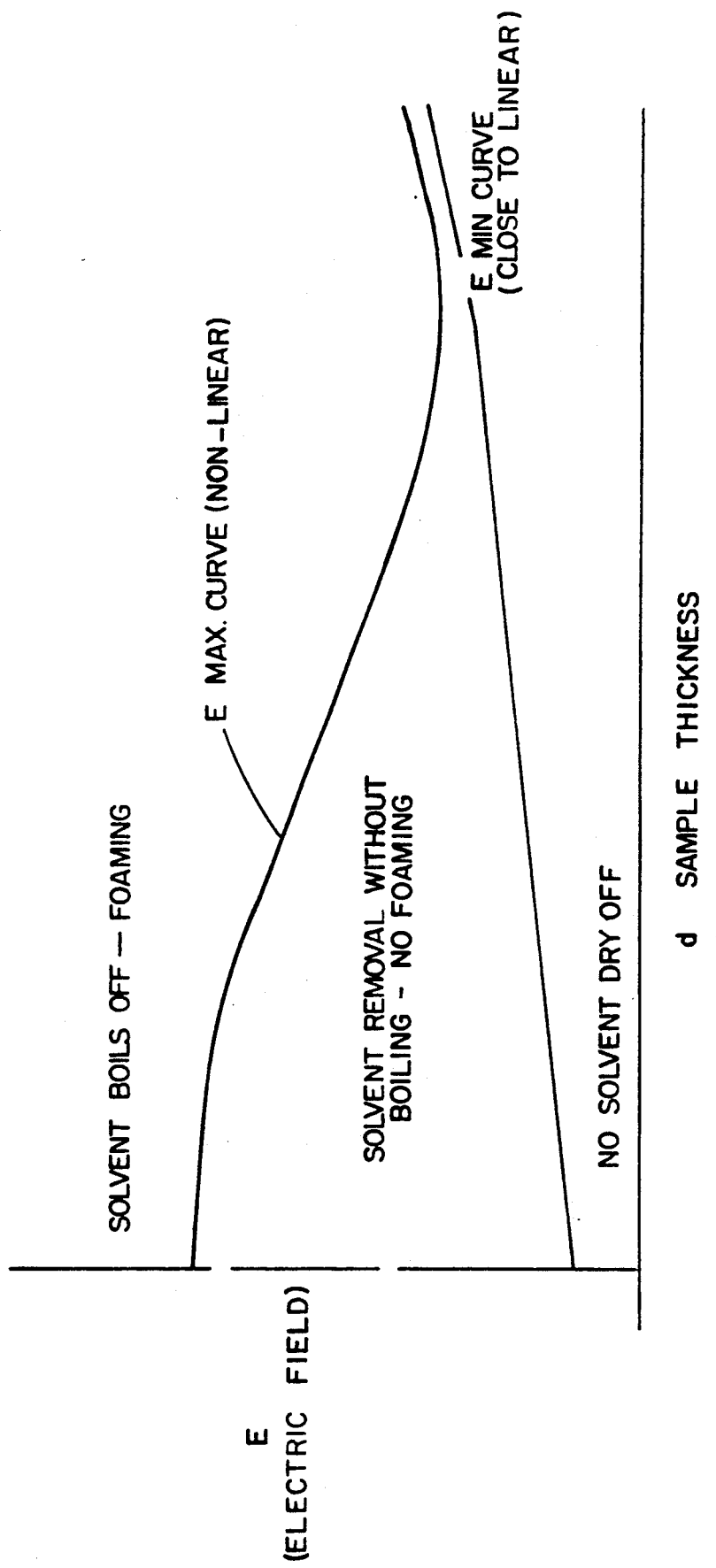
FIG. 5 comprises a plot of the electric field strength E of microwave radiation employed according to the present invention where the power of such radiation is directly related to the square of E. The electric field E is a value on the Y axis lying between E max and E min for a polyimide precursor dissolved in the solvent and is obtained by establishing where solvent removal is obtained without boiling i.e. no foaming which is a value between E min, where electric field is too small to result in solvent drying and E max, those values where the solvent boils off causing foaming of the polyamic acid at various thicknesses "d" plotted along the X axis.

Maximum properties with this type of apparatus can be obtained by varying the frequency of the microwave radiation, a sweep oscillator system being utilized in this latter respect. For example, a sample not in a cavity is exposed to microwave radiation by one or more microwave antennas similar to radar antennas. The physical parameters which control the application of microwave energy to obtain maximum results such as imidization of polyamic acid precursors or physical processes involving the removal of solvents or liquids from samples, is both the radiation frequency, (i.e. the radiation must be absorbed by the sample) and the electric field strength. The power of the radiation is related to the square of the electric field strength. A sample, such as a polyimide precursor may be disposed on a surface to form a surface layer of thickness "d." Radiation is applied which is absorbed by the sample e.g. the precursor molecules generating heat at the sites on the molecules where the radiation is absorbed. This heat flows from the points of generation thereby heating the sample. Since a thin film has a large surface area (compared to its volume), much of this heat is lost at the surface preventing the sample from reaching a temperature sufficient to remove the liquid or solvent and to continue with the process such as imidizing the precursor. Therefore, the electric field must reach a minimum value, E min, before solvent or liquid removal and subsequent processing can occur such as imidization. At the same thickness "d," if the electric field exceeds a maximum value, E max, the sample temperature will rise too fast causing the solvent or liquid in the sample to boil generating bubbles which, in the case of imidizing a polyamic acid precursor, will get trapped as the viscosity increases and the solvent is driven off. This results in foaming of the sample. Therefore, for a sample thickness "d" where E max and E min have a functional dependence on "d," as "d" increases, E max decreases because as the sample gets thicker the volatiles generated have a longer distance to travel or diffuse to the surface of the sample where the trapped gas is liberated. The E min curve increases as the sample thickness increases since the volume of the material increases with sample thickness. Power applied is proportional to $E^2$. At a given E, as the thickness increases, the power is absorbed by more material and therefore the temperature does not rise as much. Thus, as thickness increases E min must increase for the solvent to be driven off and for a subsequent imidization period. This is illustrated graphically in FIG. 5. By placing the system under vacuum, the absolute values of E min are reduced, but the principal remains valid.

After the solvent is driven off, the process proceeds during which there is a minimum E to start imidization and a maximum E beyond which the rate of generating vaporized solvent during imidization will exceed the rate of solvent diffusion out of the sample resulting in defects in the sample such as the entrapment of vaporized solvent trapped as bubbles or foam or which may cause fractures in the sample.

In conducting the imidization according to the present invention and by employing the apparatus disclosed herein it has been observed that vapor produced during the course of imidization, if not removed from the system may condense on the surface of the polyamic acid and/or polyimide being formed causing irregularities in the surface which ultimately affect the physical properties of the polyimide. In addition, the film quality, void frequency, planarity and the like are affected by solvent condensation on the film.

The vapor in this regard comprises water vapor and/or solvent that may be employed to dissolve the polyimide acid precursor, the former being present primarily because of the dehydration mechanism by which the imidization of polyamic acid proceeds to the polyamide.

Accordingly, the microwave resonant cavity is provided with means for removing the vapor by using a perforated short 10 or screen in lieu of the perforated short to allow vapor to be removed from the chamber. Ports are strategically located around the periphery of the chamber communicating with the interior thereof which may be connected to vacuum means, pressurized gas or both. The gas may be an inert gas e.g. nitrogen so that an inert atmosphere may be provided around the sample.

It has also been discovered that improved film quality can be obtained if the process is conducted so as to remove the solvent prior to actively converting the precursor into the polyimide. This is obtained by adjusting the initial power of the microwave apparatus during the process so that the temperature of the precursor is sufficiently raised to drive off the solvent as vapor at a controlled rate prior to completion of the imidization so that the precursor and the polymer that is formed is substantially free of voids and solvent. The power of the system is also adjusted to substantially prevent foaming and bubbling of the film while the vapor is being driven off so that the precursor and the polymer that is formed are non-foamed products i.e. the product obtained is substantially free of voids and solvent. Typically, precursors can be dried in two minutes as opposed to the prior art method employing a convection oven where the sample is treated at 130° C. for one hour in order to remove solvent.

The process of the invention is ideally suited for the application of a polyimide coating to any substrate and is especially adapted for coating or applying a film layer to a microcircuit or in the manufacture of sandwiched microcircuit structures. Polyimides may therefore be applied to semiconductor materials or electrical insulators and combinations of these with electrical conductors using the process and apparatus of the present invention, such process being especially adapted for the coating of alumina ceramics, glass ceramics, silica magnesium alumina, silica magnesium alumina with internal metal wiring, alumina with metal wiring and pads as well as metal lines, pads, etc. over Kapton (trademark) polyimides.

It has also been discovered according to the present invention that the process and apparatus as disclosed and described herein can be effectively used for preparing acetylene terminated polyimides in a fraction of the processing time ordinarily employed.

The key to processing the precursors for acetylene or other functionally terminated polyimides or polymers such as Thermid (trademark) 615, 601, PMR-15 (trademark) and the like (described by Bilow et al. U.S. Pat. Nos. 3,845,018; 3,864,309 and 3,879,349) lies in the ability to attain differential reactivities between the isoimide and the acetylene end groups, or the amic acid and acetylene end groups. Normally, this is accomplished by the very slow heating of the precursors. Fast heating results in the simultaneous reaction of both groups, leaving highly stressed polymeric films which have poor mechanical properties.

By employing the method and apparatus of the present invention the imidization proceeds in a controlled manner i e., the amic acid or isoimide groups on the amic acid present in Thermid (trademark 615 film have been almost totally converted to the imide form in three-five minutes without the reaction of the acetylene groups and almost complete solvent removal. The prior art methods of slowly heating these acetylene terminated polyamic acid materials resulted not only in the formation of polyimides but also the polymerization of the molecule through the acetylene groups as well. Thus, a new composition of matter is obtained in that the polyamic acid groups in this class of materials is substantially converted to a polyimide having acetylene end groups that are substantially unpolymerized and available for subsequent polymerization. This subsequent polymerization is obtained by post baking these materials in a conventional oven or microwave system, especially one having a tuneable microwave cavity or by using any other suitable heating means by which the imidization reaction is completed if not completed during the first microwave step and the acetylene end groups are reacted. Additionally, if not all of the solvent is removed in the first stage of the process it can be removed during post curing. The total processing time, (including exposing the precursor to microwave radiation according to the process of the present invention for from about three to about five minutes) is twenty minutes compared to eight hours using the prior art method The retention of mechanical properties of these acetylene terminated polyimides that are subsequently cured according to the process of the present invention can be observed from the DMTA chromatograms and stress-strain analysis, in which such materials are compared with a sample that is cured by conventional thermal means. The glass transition temperature is the same (within experimental error), the initial modulus is the same and the modulus above the glass transition temperature is the same. Furthermore, it is observed that Tg increases upon prolonged exposure to 400° C. is exactly the same at 4C/hour at 400C, indicating that the accelerated curing cycle of the present invention for this class of acetylene terminated polyimides is not detrimental to the mechanical properties of this material, which is not the case when a very fast, high temperature thermal cure is used. Furthermore, the elongation at failure is the same, indicative of similar toughness between the microwave sample of the present and the slow thermal sample of the prior art.

Referring to the drawings, FIG. 1 illustrates a tuneable microwave resonant cavity apparatus 2 according to the present invention comprising cylindrical sidewall 4 with a topwall enclosure 6 and a bottom enclosure 2 having an inner surface on which a sample of polyamic acid precursor may be positioned. The apparatus 2 is also vented by means of opening 9 and nipples 29 in sidewall 4. A plate 10 is arranged to slidably engage the inner surface of sidewall 4 and has a sliding seal 11 positioned at the periphery thereof. Sidewall 4 may be constructed of stainless steel, the inner surface of which is highly polished so that it will more effectively reflect microwave radiation. The inner surface of said sidewall 4 may also be coated with a material that is highly reflective to microwave radiation but is also resistant to oxidation such as gold, silver-gold alloys and the like. The plate 10 is referred to as a "short" and has apertures 12 arranged throughout it so that any vapor in the chambers defined above and below short 10, sidewall 4, topwall 6 and bottom wall 8 can pass through such apertures. A screen, which will also function as a short, may be used in lieu of plate 10. A conduit 20 is connected by means of nipples 29 through sidewall 4 and opens into the chamber formed between sidewall 4, short 10 and bottom plate 8. Control rods 14 are securely attached to short 10 and held in a fixed spaced relationship relative to one another by means of plate 16 having opening 18 therein, control rods 14 being slidably moveable through topwall 6 by apertures therein arranged to slidably receive control rods 14. A microwave probe 22 is slidably mounted in the base of sidewall 4 so that it may be moved in or out of the chamber defined between the bottom face of short 10 and the bottom wall 8 and sidewall 4 by means of rack 24 and pinion 26 or a threaded screw assembly operatively associated with a prime mover 28 which may be operated manually or by an electric motor controlled by a computer or manual controls. The microwave probe 22 is operatively connected at its exterior end (i.e. that end which does not project into the apparatus 2) to a microwave supply as will be further understood by reference to FIG. 2, the latter illustrating a microwave processing system 30.

The microwave power can be anywhere from 5 to 1,000 watts and especially 50 to 600 watts. A 500 watt power supply is typically used in one embodiment of the invention. Any frequency from 300 MHz to 120 GHz can be used as the microwave frequency of the microwave apparatus; specific useable frequencies are 915 MHz, 2450 MHz and 28 GHz.

Figure 2:
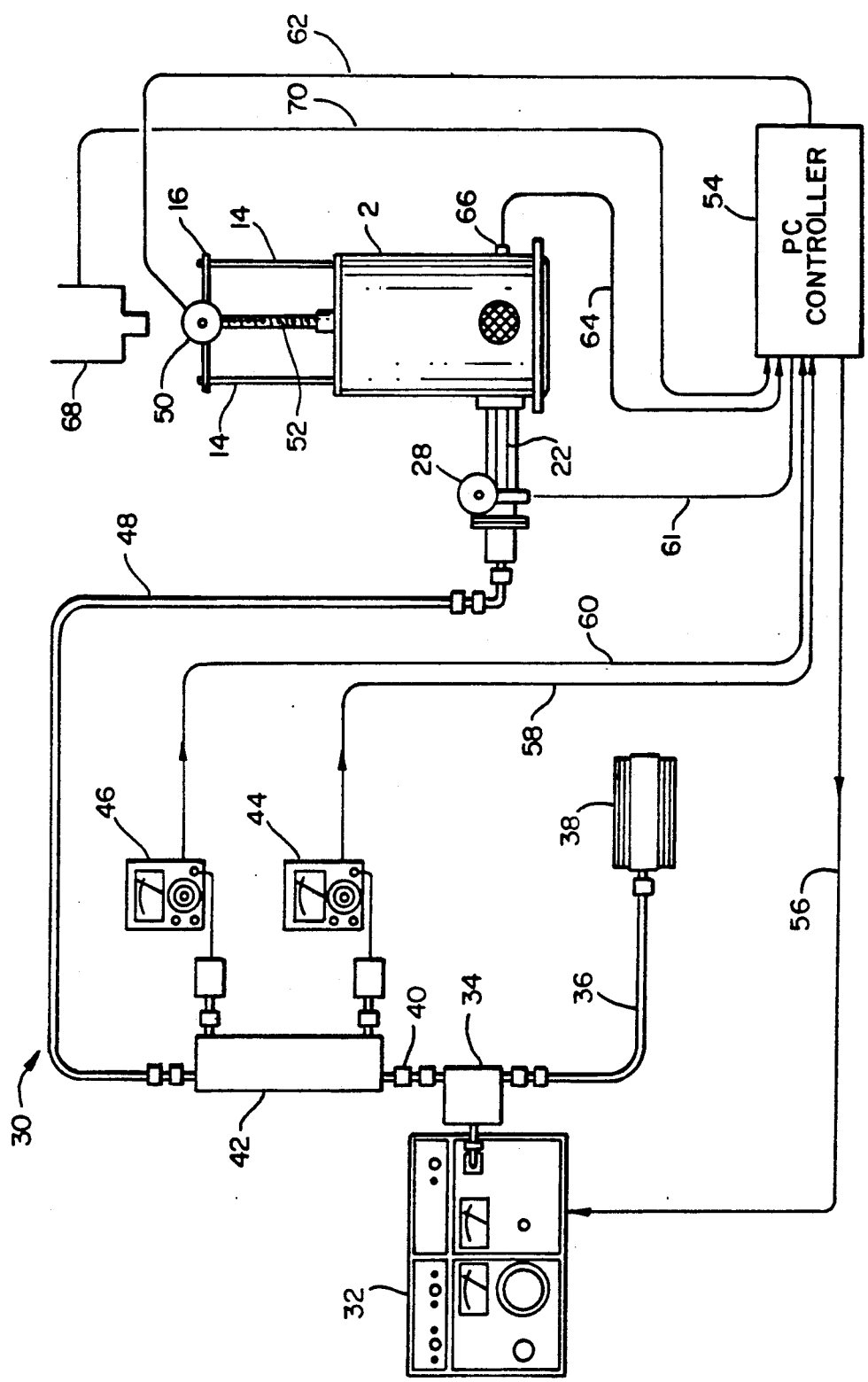
FIG. 2 comprises a flow diagram illustrating the connection to the tuneable microwave cavity of a microwave supply, three port circulator, directional coupler, power meters, dummy load, pyrometer and computer controller for monitoring power output, temperature of the microwave cavity and the Q factor of the microwave cavity.

The microwave processing system 30 of FIG. 2 illustrates a microwave supply 32 such as Micro-Now (trademark) model 420B1 operatively associated with a three port circulator 34 such as Ferrite control No. 2620. The three port circulator 34 has a dummy load 38 such as NARDA 368BN operatively associated therewith by connector 36. The three port circulator 34 is also operatively connected to directional coupler 42 such as NARDA 3043D which in turn is operatively associated with power meters and sensors 44 and 46 such as a Hewlett Packard HP 435 device. Directional coupler 42 in turn is operatively associated with the microwave probe 22 by means of coaxial cable or moved upwardly and downwardly within the device 2 by means of prime mover (e.g. electric motor) 50 operatively associated with a worm drive 52 in a manner known in the art. A controller 54 comprising a programmed computer is operatively associated with microwave supply 32 by means of conduit 56, power meters and sensors 44 and 46 by conduit 58 and 60, prime mover 28 by conduit 61, prime mover 50 by means of conduit 62 and thermocouple 66 and optical pyrometer 68 by means of conduits 64 and 70 respectively.

Figure 3:
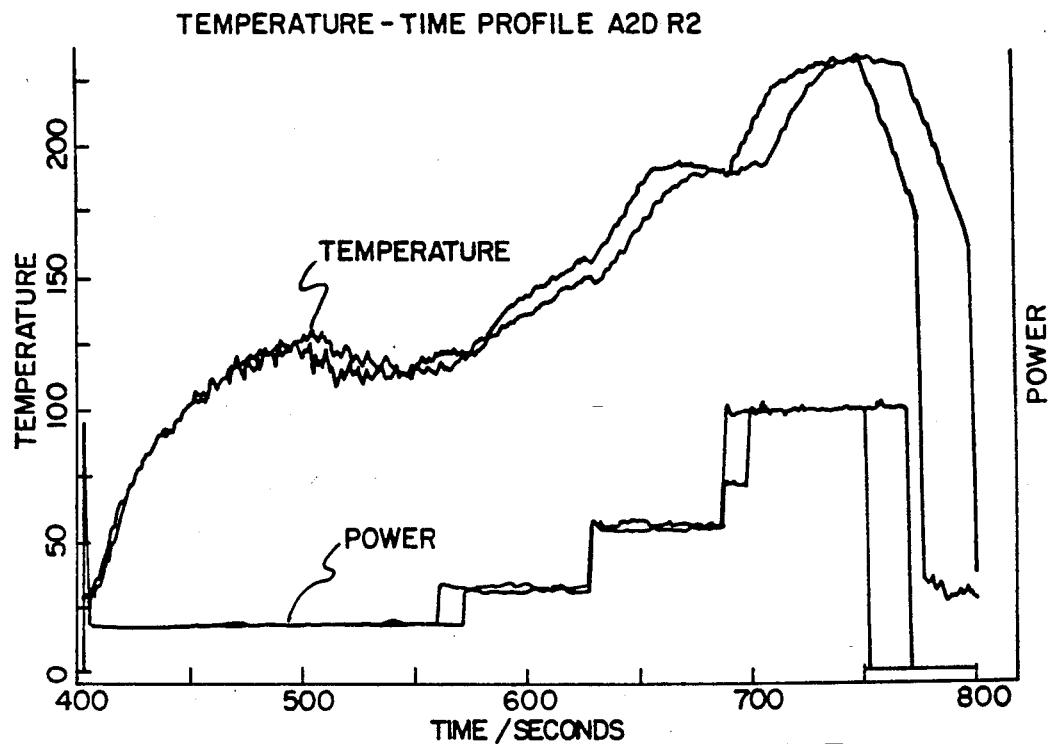
FIG. 3 is a plot of microwave power (Y axis) against time (X axis) applied to the microwave cavity of FIG. 1 and the resultant temperature of the precursor and/or polymer obtained over the period of time such power is applied.

In use, and referring to FIGS. 1 and 2, a polyamic acid precursor is dissolved in a solvent and coated on a base such as a micro circuit and the microcircuit thus coated positioned within the cavity between bottom wall 8, sidewall 4 and short 10 of apparatus 2. The microwave supply 32 is turned on and microwave radiation is caused to radiate from probe 22 within the chamber of apparatus 2 probe 22 being moved in or out of the chamber to match the impedance of the system as the dielectric constant of the system changes. The power is controlled by the programmed controller 54 in response to the temperature of the sample in the chamber 2 as measured by pyrometer 68 and the temperature of the cavity as monitored by IR pyrometer 66 or an equivalent thereof. The reflected power from the apparatus 2 is measured by power meters and sensors 44 and 46 which in turn relay this information to the controller 54 which conveys a programmed response to the prime mover 50 so that the short 10 may be moved upwardly or downwardly and the probe 22 moved in and out of the microwave resonant cavity within the apparatus 2, so it may be tuned to achieve minimum reflected power and hence critical coupling for the system, as the system is defined herein. The controller 54 is programmed, in one instance to provide power to the apparatus in a manner to obtain the temperature over the time period as illustrated in FIG. 3. The application of power to attain the temperatures as set forth in FIG. 3 and movement of the short to attain the critical coupling may also be effected manually rather than by utilization of controller 54.

The invention also relates to algorithms which have been developed that allow the computer to maintain cavity resonance by monitoring the reflected microwave power and acting so as to minimize the reflected power by the adjustment of the sliding short 10 and the input probe 22.

Initially, an algorithm programmed into controller 54 causes the sliding short 10 to be returned to a "home" position below the desired resonance. Short 10 is then raised in a step wise manner followed by reading the reflected power after each step on meters 44 and 46. When the reflected power decreases below a threshold value, indicating an approach to a resonance dip as illustrated in FIG. 4, the step size is reduced and the direction of the step is now controlled depending on the sign of the difference between the last two data points and the absolute position of the short where those two power values were measured. As the reflected power continues to decrease below other thresholds, the step size is further reduced. If the reflected power reaches a local minimum, the computer program in controller 54 produces a signal which causes the movement of the input probe 22 so as to match the impedance of the cavity, using a similar difference between the reflected power and absolute position to determine in which direction to move.

This routine is capable of reducing the microwave power to less than 0.1 percent of the forward power reflected from the cavity. More importantly, the routine "tracks" a curing polymer system, resulting in the system maintaining resonance during the complete processing cycle.

A second algorithm programmed into controller 54 requires the short 10 to move over a large distance, passing the resonance dip, while recording the level of the reflected power and then returning the short to the position where the minimum was found. If reflected power is not zero, a similar routine, generated by processor 54 operates on the input probe 22 to find a minimum for that axis and program execution returns to find the position of the reflected power minimum for the short period. This iteration continues until the reflected power is zero. Either this second routine or the above first routine can then be invoked to maintain resonance for the remainder of the processing cycle.

Typically these routines take only about 15 seconds to find resonance.

A feature of apparatus 2 comprises means for removing vapor from the chamber thereof so that such vapor (e.g. solvent and/or water) will not condense and redeposit on the sample being processed. As illustrated in FIG. 1, apertures 12 are provided which allow vapor developed during processing of a sample in the chamber below short 10 (as that chamber is defined herein) to pass into the upper chamber and either condense in the upper chamber or to be vented through an opening in plate 6 or by means of conduit 20 which optionally is operaively associated with a vacuum pump to more completely evacuate the chamber below short 10. Opening 9 at the bottom of sidewall 4 or nipples 29 allows for an external fluid such as dry purified dust-free air or similar gas to enter the bottom of the apparatus 2 and be withdrawn through conduit 20. Optionally, short 10 can comprise a non-perforate plate (i.e. a plate without any openings therein) and the apparatus 2 can be evacuated by a series of conduits strategically placed along the length of sidewall 4 and operated simultaneously or serially to evacuate the chamber above or below short 10 as those chambers are being varied in volume depending on the movement of short 10 upwardly or downwardly along the inner surface of sidewall 4.

The opening 18 in the plate 16 is provided so that the pyrometer 68 may be focused on the sample through an opening in top wall 6 and short 10 that is aligned with opening 18 and through which the optical pyrometer 68 may be aimed. A fiber optic temperature probe may be used in lieu of the pyrometer and focused on the sample through an opening in the sidewall 4 rather than from above.

Although the invention has been described by reference to some embodiments it is not intended that the novel process and apparatus be limited thereby but that certain modifications are intended to be included as falling within the spirit and broad scope of the foregoing disclosure, the following claims and attached drawings.

We claim:

1. A method for manufacturing a polyimide comprising irradiating a polyimide precursor containing polyamic acid groups or polyamic acid ester groups or isoimide groups by a microwave apparatus means for applying microwave radiation to said precursor, said means having a variable power output, said precursor being combined with a solvent, said precursor in combination with said microwave apparatus means comprising a system, said radiation being applied to substantially completely remove said solvent and imidize said precursor to said polyimide, and adjusting the power of said microwave radiation and maintaining resonance of said microwave radiation in said system during said imidization to control the degree and rate of said solvent removal and said imidization of said precursor to said polyimide to obtain a substantially defect free polyimide.

2. The method of claim 1 where said apparatus s a tuneable microwave resonant cavity.

3. The method of claim 1 where said precursor also contains polymerizable acetylene terminal groups and said imidization is conducted so as to leave said terminal groups substantially unpolymerized.

4. The method of claim 2 where said precursor also contains polymerizable acetylene terminal groups and said imidization is conducted so as to leave said terminal groups substantially unpolymerized.

5. The method of claim 3 where said imidization is effected by said microwave radiation so that said polyimide is substantially free of polyamic acid groups, polyamic acid ester groups and isoimide groups.

6. The method of claim 4 where said imidization is effected by said microwave radiation so that said polyimide is substantially free of polyamic acid groups.

7. The method of claim 1 where any vapor produced in said system during said imidization is removed from said system.

8. The method of claim 7 where said vapor is removed to a sufficient degree so that it does not condense as a liquid on the surface of any polyimide formed.

9. The method of claim 1 where said precursor is in a solvent prior to imidization, said precursor being initially exposed to microwave radiation sufficient to drive off said solvent as vapor prior to completion of said imidization so that said precursor and the polymer that is formed is substantially free of voids and solvent.

10. The method of claim 9 where the power of said system is adjusted to substantially prevent foaming while said vapor is being driven off so that said precursor and said polymer that is formed is substantially free of voids and said solvent.

11. The method of claim 10 where said vapor is removed from said system before said imidization is completed.

12. The method of claim 1 where said precursor is a film supported on a substrate.

13. The method of claim 12 where said substrate comprises a microcircuit.

14. The method of claim 12 where said substrate comprises a semiconductor material.

15. The method of claim 12 where said substrate comprises an electrical insulator.

16. The method of claim 1 comprising:
said polyimide precursor being a film of a predetermined thickness;
exposing said film to said microwave radiation where said radiation has a wavelength sufficient to be absorbed by said film;
the electric field of said radiation having a value sufficient to cure said precursor to a substantially defect free polyimide film.

17. The method of claim 16 where said electric field is selected between E max and E min and is dependent on said predetermined thickness.

18. A method for manufacturing a polyimide comprising irradiating a polyimide precursor containing polyamic acid groups or polyamic acid ester groups or isoimide groups by a microwave apparatus means for applying microwave radiation to said precursor, said means having a variable power output,
said precursor in combination with said microwave apparatus means comprising a system,
said radiation being applied to imidize said precursor to said polyimide,
and adjusting the power of said microwave radiation while maintaining resonance of said microwave radiation in said system during said imidization to control the degree and rate of said imidization of said precursor to said polyimide to obtain a substantially defect free polyimide.

19. The method of claim 18 where said apparatus comprises a tuneable microwave resonant cavity.

20. The method of claim 18 wherein said precursor also contains polymerizable acetylene terminal groups and said imidization is conducted so as to leave said terminal groups substantially unpolymerized.

21. The method of claim 19 where said precursor also contains polymerizable acetylene terminal groups and said imidization is conducted so as to leave said terminal groups substantially unpolymerized.

22. The method of claim 20 where said imidization is effected by said microwave radiation so that said polyimide is substantially free of polyamic acid groups or polyamic acid ester groups or isoimide groups.

23. The method of claim 19 where said precursor is a film supported on a substrate.

24. The method of claim 23 where said substrate comprises a microcircuit.

25. The method of claim 23 where said substrate comprises a semiconductor material.

26. The method of claim 23 where said substrate comprises an electrical insulator.

27. The method of claim 23 where said substrate comprises a metal containing substrate.

28. The method of claim 23 where said precursor contains polyamic acid and said substrate comprises a metal containing substrate.

* * * * *

UNITED STATES PATENT AND TRADEMARK OFFICE
CERTIFICATE OF CORRECTION

PATENT NO. : 5,317,081

DATED : May 31, 1994

INVENTOR(S) : Jerome D. Gelorme, et al.

It is certified that error appears in the above-indentified patent and that said Letters Patent is hereby corrected as shown below:

Column 1, line 62: "radiate" should read --radiation--

Column 2, line 9: "4,681,655" should read --4,681,654--

Column 2, line 20: after "the" insert --curing.--

Column 3, line 43: after "e.g. the" insert --cavity, the substrate on which the precursor is mounted,--

Column 5, line 32: after "Gagliani" delete --.--

Column 6, line 2: after "a" insert --minimum--

Column 6, line 60: after "to" insert --provide a method and apparatus for manufacturing polyimides--

Column 7, line 6: "e" should read --be--

Column 8, line 33: "whither" should read --whether--

Column 8, line 50: after "products of" insert --reaction (alcohols and/or water in the case of the--

Column 9, line 12: before "of" insert --to a tuneable microwave cavity whereby the resonance --

UNITED STATES PATENT AND TRADEMARK OFFICE
CERTIFICATE OF CORRECTION

PATENT NO. : 5,317,081
DATED : May 31, 1994
INVENTOR(S) : Jerome D. Gelorme, et al.

It is certified that error appears in the above-indentified patent and that said Letters Patent is hereby corrected as shown below:

Column 11, line 45: after "method" insert --.--
Column 12, line 1: "2" should read --8--
Column 12, line 56: "4043 D" should read --3043 B--
Column 12, line 60: after "or" insert --suitable waveguide 48. The short 10 as described in Fig. 1 is--
Column 14, line 23: "operaively" should read --operatively--
Column 15, line 4, Claim 2; delete "s a" and insert --comprises--

Signed and Sealed this

Third Day of January, 1995

Attest:

BRUCE LEHMAN

*Attesting Officer*   *Commissioner of Patents and Trademarks*